US008900201B2

(12) United States Patent
Edhouse et al.

(10) Patent No.: US 8,900,201 B2
(45) Date of Patent: Dec. 2, 2014

(54) DEVICE FOR THE AUTOMATIC INJECTION OF TWO DOSES OF A MEDICAMENT

(75) Inventors: Mark Jeffrey Edhouse, Cambridge (GB); Philip Jerome Driver, Cambridge (GB); Guy Conwyn Julian Moseley, Waterbeach (GB); Scott Alexander Lewis, Cambridge (GB)

(73) Assignee: Menarini International Operations Luxembourg S.A., Luxembourg (LU)

( * ) Notice: Subject to any disclaimer, the term of this patent is extended or adjusted under 35 U.S.C. 154(b) by 0 days.

(21) Appl. No.: 14/342,622

(22) PCT Filed: Sep. 6, 2012

(86) PCT No.: PCT/EP2012/067431
§ 371 (c)(1),
(2), (4) Date: Mar. 4, 2014

(87) PCT Pub. No.: WO2013/034647
PCT Pub. Date: Mar. 14, 2013

(65) Prior Publication Data
US 2014/0221936 A1    Aug. 7, 2014

(30) Foreign Application Priority Data
Sep. 8, 2011   (IT) .............................. FI2011A0193

(51) Int. Cl.
*A61M 5/32*     (2006.01)
*A61M 5/20*     (2006.01)
*A61M 5/315*    (2006.01)
*A61M 5/00*     (2006.01)
*A61M 5/31*     (2006.01)
*A61M 5/178*    (2006.01)

(52) U.S. Cl.
CPC ............ *A61M 5/20* (2013.01); *A61M 5/31525* (2013.01); *A61M 5/31585* (2013.01); *A61M 5/31593* (2013.01); *A61M 5/326* (2013.01); *A61M 5/31533* (2013.01); *A61M 5/002* (2013.01); *A61M 5/3204* (2013.01); *A61M 2005/2013* (2013.01); *A61M 2005/3104* (2013.01); *A61M 2005/1787* (2013.01); *A61M 2005/206* (2013.01); *A61M 2005/31588* (2013.01)
USPC ............................ 604/198; 604/134; 604/137

(58) Field of Classification Search
USPC ................. 604/181, 182, 137, 134, 135, 186, 604/208–211, 131, 187, 192, 233, 198
See application file for complete search history.

(56) References Cited

U.S. PATENT DOCUMENTS

| 4,031,893 A | 6/1977 | Kaplan et al. |
| 5,665,071 A | 9/1997 | Wyrick |

(Continued)

FOREIGN PATENT DOCUMENTS

| EP | 651662 | 10/1995 |
| EP | 0700307 | 3/1996 |
| WO | 94/26331 | 11/1994 |
| WO | 94/27660 | 12/1994 |
| WO | 2009/040602 | 2/2009 |

OTHER PUBLICATIONS

PCT International Search Report mailed on Sep. 5, 2011 for PCT/IB2011/050985 filed on Mar. 9, 2011 in the name of Menarini International Operations Luxembourg S.A.

(Continued)

*Primary Examiner* — Nicholas Lucchesi
*Assistant Examiner* — Weng Lee
(74) *Attorney, Agent, or Firm* — Steinfl & Bruno LLP

(57) ABSTRACT

A device for the automatic injection of doses of a drug is described. The device has a slide and cam means, a syringe unit with a piston, and guide means. The axial movement of the slide initiated by a user by depressing its front end against an injection site, causes an angular displacement of the cam means that, in cooperation with the guide means, controls movement of the syringe piston and therefore administration of a drug dose.

17 Claims, 11 Drawing Sheets

(56) References Cited

U.S. PATENT DOCUMENTS 6,575,939 B1    6/2003    Brunel
8,357,125 B2 *   1/2013    Grunhut et al. ............... 604/240

OTHER PUBLICATIONS

PCT Written Opinion mailed on Sep. 5, 2011 for PCT/IB2011/050985 filed on Mar. 9, 2011 in the name of Menarini International Operations Luxembourg S.A.

PCT International Search Report mailed on Dec. 17, 2012 for PCT/EP2012/067438 filed on Sep. 6, 2012 in the name of Menarini International Operations Luxembourg S.A.

PCT Written Opinion mailed on Dec. 17, 2012 for PCT/EP2012/067438 filed on Sep. 6, 2012 in the name of Menarini International Operations Luxembourg S.A.

PCT International Search Report mailed on Dec. 17, 2012 for PCT/EP2012/067431 filed on Sep. 6, 2012 in the name of Menarini International Operations Luxembourg S.A.

PCT Written Opinion mailed on Dec. 17, 2012 for PCT/EP2012/067431 filed on Sep. 6, 2012 in the name of Menarini International Operations Luxembourg S.A.

\* cited by examiner

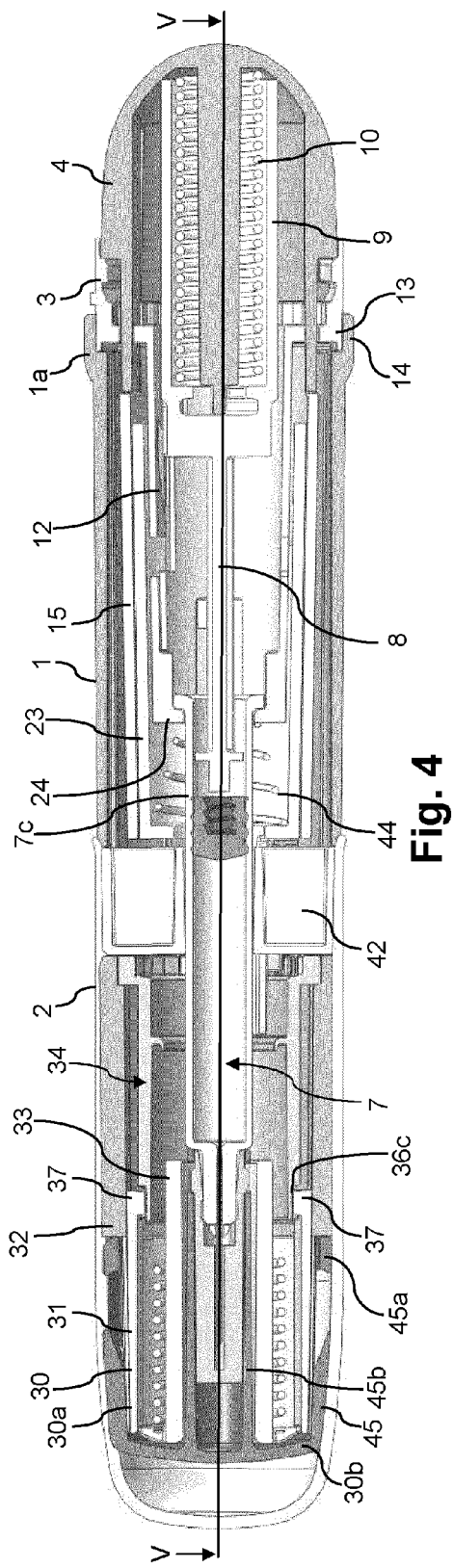
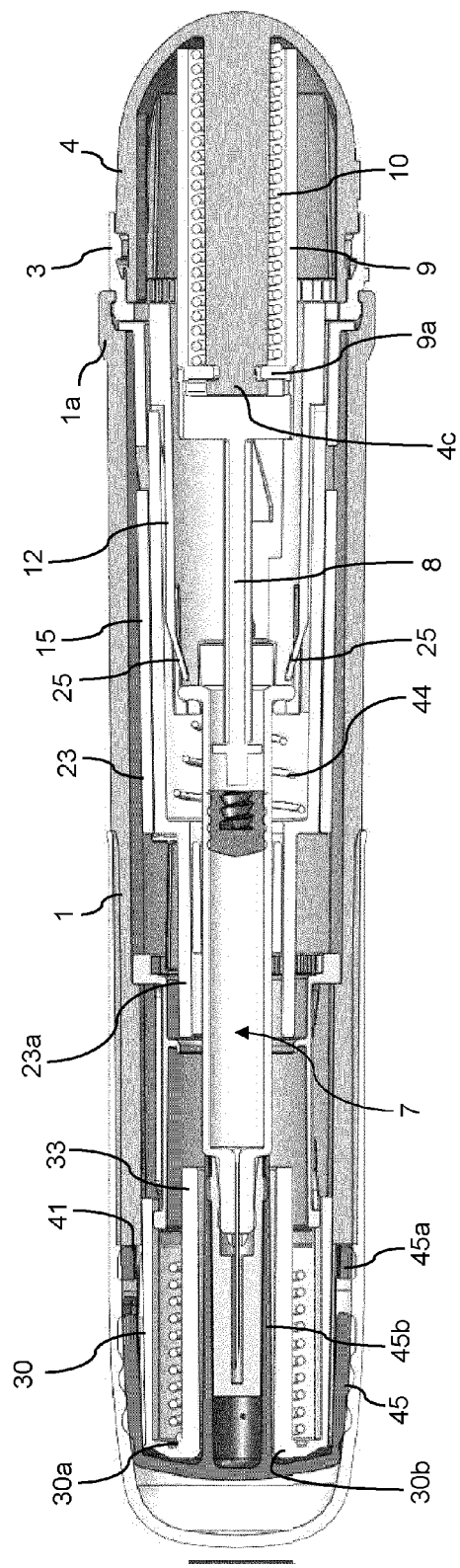
Fig. 4
Fig. 5

DEVICE FOR THE AUTOMATIC INJECTION OF TWO DOSES OF A MEDICAMENT

CROSS REFERENCE TO RELATED APPLICATIONS

The present application is the US national stage of International Patent Application PCT/EP2012/067431 filed on Sep. 6, 2012 which, in turn, claims priority to Italian Patent Application FI2011A000193 filed on Sep. 8, 2011.

FIELD OF THE INVENTION

The present invention relates generally to devices for the injection of medicaments and more precisely relates to a device for the automatic injection of medicaments especially a medicament for allergic emergencies, such as epinephrine or adrenaline, according to a requested time sequence. In particular, the invention refers to a device for the automatic injection of two doses of a medicament at two successive times.

BACKGROUND OF THE INVENTION

Many devices of the above mentioned type allowing a patient to self-administer one or more (generally two) doses of a medicament are known. U.S. Pat. No. 6,575,939 discloses an autoinjector device comprising a syringe housed in a casing formed by an inner part and an outer part capable of sliding in relation to each other. By pressing the end of the inner part (the needle outlet end) against the patient's skin at the injection site, the outer part slides forward along the inner part, thus unlocking a push-button. By depressing the button, the syringe and the relevant plunger are triggered to first thrust in the needle and then deliver the medicament. The needle retraction in the casing is obtained by stopping pressing the outer part end against the skin. This auto-injector allows a single dose of medicament to be administered.

An autoinjector device for automatic administering a single dose of a medicament is also known from U.S. Pat. No. 4,031,893. The autoinjector is equipped with an unlocking device with a deformable member for the driving device. The syringe plunger is axially connected to a rod comprising four flexible axial arms having a toothed end engaged on the edge of an opening formed on a cap placed at the end of the syringe housing. Cap sliding causes the arm ends to deform and their teeth to release from the opening edge. In this way the driving device is triggered. The autoinjector according to this document also comprises a safety device to prevent accidental deformation of the arm ends and triggering of the driving device, consisting of an insert centrally extending from the cap and capable of coming between the rod arms to prevent them from bending.

EP 700 307 discloses a two-dose autoinjector allowing the automatic delivering of a first dose of a medicament and the manual administration of a second dose. The autoinjector device according to this patent foresees the use of a syringe housed slidably in a tubular housing in two parts that can be separated to allow positioning of the syringe containing two doses of the medicament to be delivered and removal after use. The sliding of the syringe in the housing to penetrate the needle and inject the medicament is operated by an actuator movable between an armed position and an extended position. A releasable locking device is provided to limit the syringe plunger sliding to an extent corresponding to the volume of the first dose. The syringe is mounted in the tubular housing in a movable way to enable the locking device to be removed after the first dose is delivered and the plunger drive means to be armed again, if the second dose is to be automatically administered, or the syringe to be removed, if the second dose is to be manually administered. Furthermore the drive means is provided with a safety lock formed by a member engaging with a deformable pin of the drive means to keep it in a deformed condition, thereby preventing it to trigger. An autoinjector of this type is commercially available under the trade mark Twinject® and allows the first dose to be administered automatically, but the second dose must be manually administered.

The autoinjector according to EP 651 662 is designed to carry out a sequence of injections from a single syringe that is capable of performing a limited sliding movement in a tubular housing. The syringe has a plunger to deliver doses of a medicine through the needle and spring drive means engage with a piston rod and, once they are armed, retain the rod in a first position, while, when they are triggered, cause the rod to move forward and this causes first the syringe sliding and needle projection and then a controlled sliding of the plunger to deliver a medicine dose. Manual arming means are provided and means to trigger again the spring drive means.

The plunger rod has a toothed profile on which a catch of the drive means engages and the syringe is housed in a bushing capable of moving in a limited way in the tubular housing and provided with a further catch that is also engaged with the toothed profile of the rod. When the device is armed by the manual arming means, both the drive means and the bushing in which the syringe is placed are displaced toward the rear end of the tubular housing, the two catches engaging with the toothed profile of the rod. An axial groove connection between the bushing and the drive means allows a further sliding between the catch integral to the drive means and the toothed profile of an extent equal to the pitch of the profile. When the device is triggered, first the drive means cause the syringe bushing to slide up to a front stop and then the rod start sliding relative to the bushing catch for an extent corresponding to the profile pitch, whereby the displacement of a volume of medicine is enabled together with its deliver through the needle.

There is a strong need for an injector device for the automatic injection of a medicament in two successive doses which is user-friendly and is easier to manufacture as compared to the conventional devices. The subject of the present invention is therefore to meet these requirements by providing a medicament autoinjector device capable of enabling the patient to self-administering at least two successive doses of a medicament in the easiest possible way, thus sparing the patient of performing potentially dangerous, complex dismounting/re-arming operations.

SUMMARY OF THE INVENTION

The general subject of the present invention is to provide a device for the automatic injection of multiple discrete nominal volumes of a drug compound, in particular of two doses of the drug compound from the same syringe.

A particular subject of the present invention is to provide a device of the above mentioned type in which the automatic injection of discrete nominal volumes of drug product is achieved by a combination of rotational and translational movements of the device components.

A further subject of the present invention is to provide a device of the above mentioned type in which the automatic injection of a prescribed dose is triggered by the use of a linear sliding of a component activated by the patient, in combination with the angular displacement of plunger means being guided by cam means in an encapsulated chassis.

It is a further subject of the present invention to provide a device of the above mentioned type with an automatic sheathing lock-out feature for needle protection and prevention of inadvertent triggering of the device before a dose is selected by the user.

Still another subject of the present invention is to provide a device of the above mentioned type capable of automatic re-sheathing the needle and resetting the lock-out condition after a dose is injected.

It is still another subject of the present invention to provide a device of the above mentioned type wherein the user is required to apply a certain force to expose the needle, but thereafter a quick insertion of the needle in the patient is aided.

A further subject of the present invention is to provide a device of the above mentioned type in which the steps required to the user to initialize the device are minimized, in particular limited to the rotation of only one component to activate the delivery of a dose of drug.

The above subjects are achieved with the device for the automatic injection of doses of a medicament according to the present invention, whose main features are set forth in the attached claim 1. Further important features are set forth in the dependent claims.

According to an important aspect of the device for the automatic injection of doses of a drug according to the present invention, the axial movement of a slide, caused by the user by depressing its front end against the injection site, causes the angular displacement of cam means, which, in cooperation with stepped guide means, controls the movement of plunger means of a syringe group and thus the delivery of prefixed doses of the drug. The movement of the plunger means is produced by axially operating first elastic means, while the axial movement of the sliding sheath is hindered by second elastic means that reinstate the initial needle covering condition of the slide when the pressure action ceases. To make the device ready for the delivery of a dose, device arming means are provided which, when operated, unlock the slide axial movement. The lock-out condition, as well as the needle retraction in the slide, are automatically reinstated when the pressure ceases under the action of the second elastic means.

According to another important aspect of the invention the guide means for the plunger means are formed on an inner body integral to the outer body of the device and the cam means for triggering the device are formed on a transmission sleeve interacting with the slide at one side and with the inner body and the selection sleeve at the other side. In this way, a slide movement results in a sliding and an angular displacement of the transmission sleeve driven by the inner body for the first dose delivery and by the selection sleeve for the second dose delivery.

BRIEF DESCRIPTION OF THE DRAWINGS

Further features and advantages of the auto-injector device according to the invention will be apparent from the following description of an exemplifying, non-limiting embodiment thereof with reference to the attached drawings, in which:

FIG. 4 is a longitudinal section of the device of FIG. 1;

FIG. 5 is a longitudinal section of the device of FIG. 1 taken along lines V-V of FIG. 4;

DETAILED DESCRIPTION OF THE INVENTION

Figure 1:
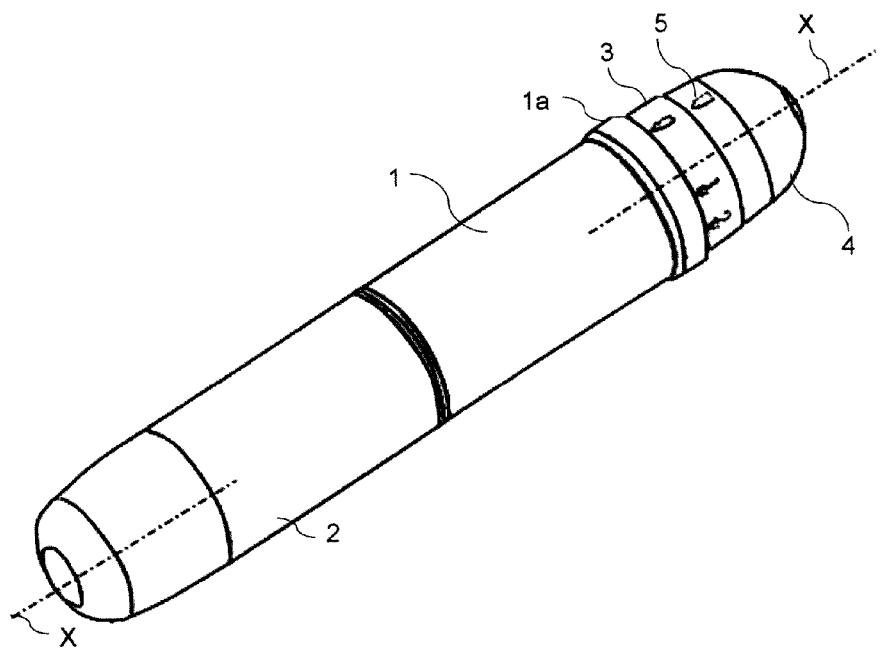
FIG. 1 is an overall view of the auto-injector device according to the present invention.
Figure 2:
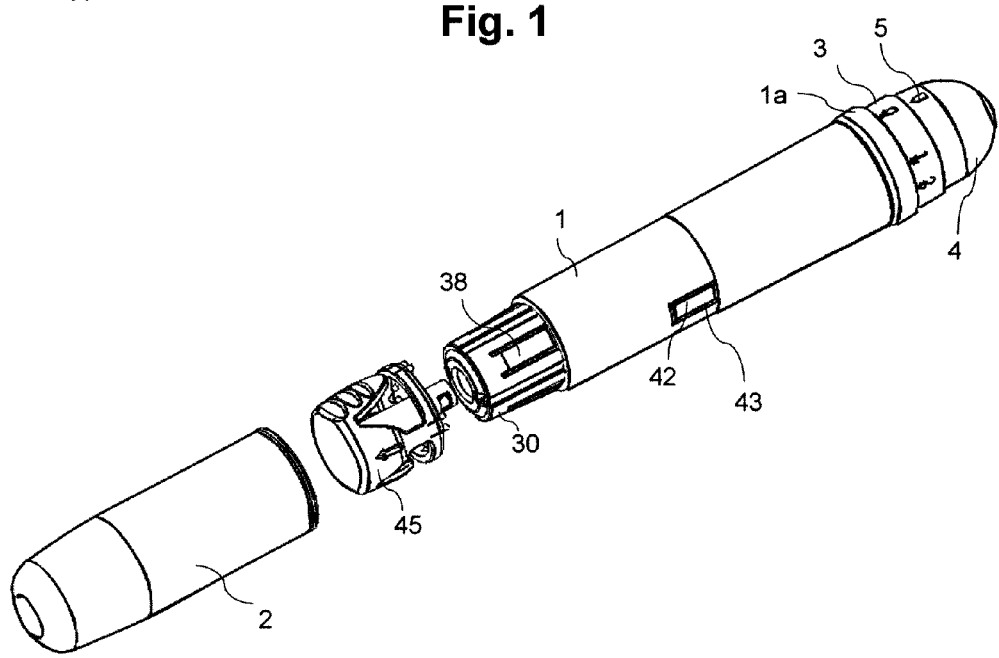
FIG. 2 is a partially exploded, perspective view of the device of FIG. 1.
Figure 3:
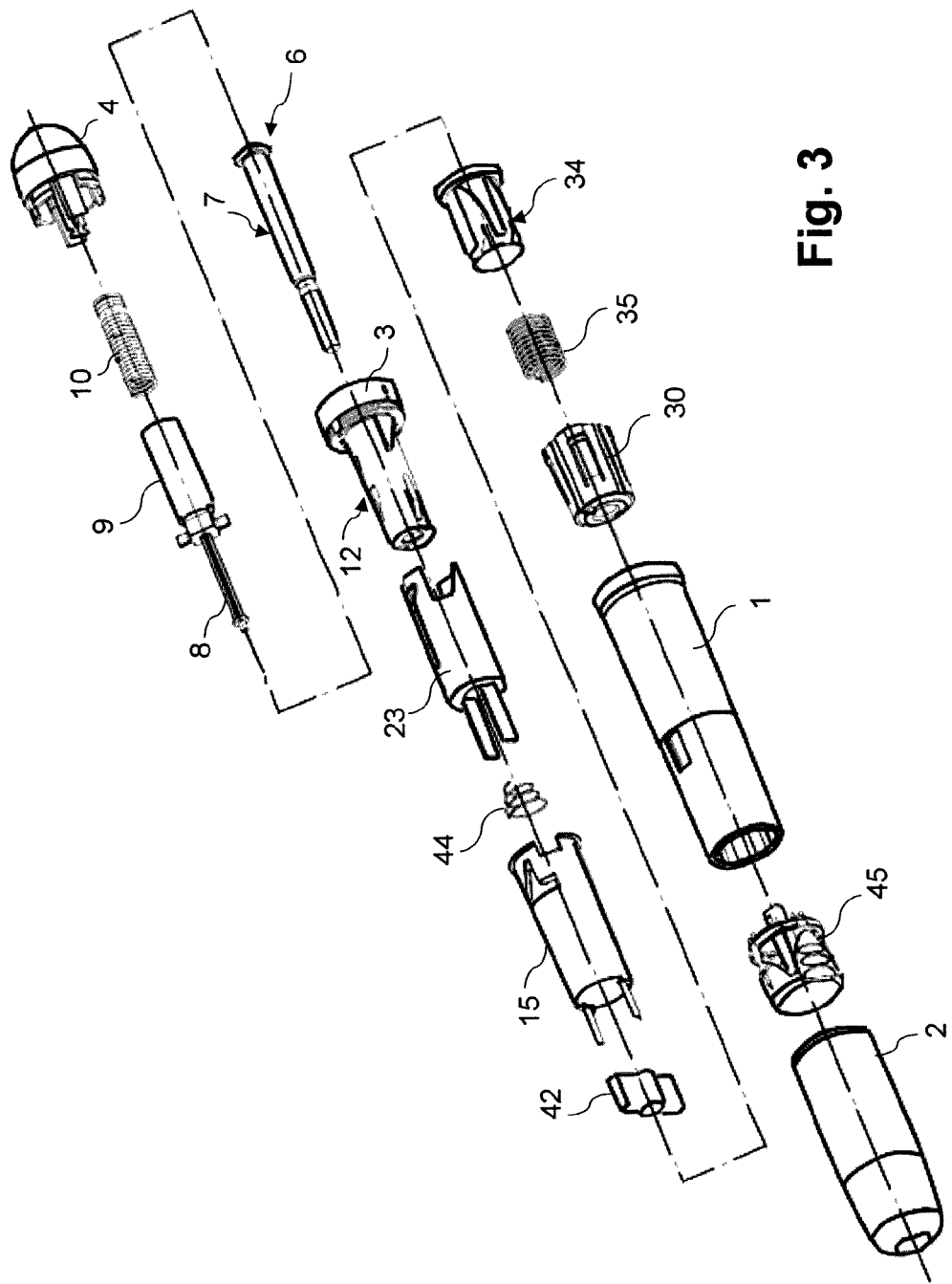
FIG. 3 is a fully exploded view of the device of FIG. 1.

With reference to FIGS. 1-5, the autoinjector device according to the present invention comprises an outer body 1 of tubular shape, in particular a cylindrical shape, extending along an axis X and containing the majority of the device components within it. The outer body 1 is closed at its front end by a removable cap 2, while from its rear end, enlarged by a flange 1a, there projects a collar 3, on which angularly spaced reference marks, in particular the numerals 0, 1, 2, are shown, indicating a rest state (0) and two operating states (1, 2) of the device, as explained later on. In the present description the terms "front", "rear" and equivalents relate to the part of the device intended for the needle outlet and, respectively, the axially opposed part. It is also stated that in the present description reference is always made to a device for the automatic injection of two doses of a drug, but it is understood that the invention also comprises devices capable of delivering more than two doses of a drug at successive times, through changes and alteration to the device which are obvious for a person skilled in the art.

A dose selection knob 4 on which a reference arrow 5 is shown extends from the collar 3. The knob 4 is axially rotatable relative to the collar 3 to allow the arrow 5 to align to the reference marks shown on the collar 3.

A syringe unit, generally indicated as 6, is housed in the outer body 1 and comprises a drug pre-filled syringe 7 with relevant needle 7a, needle shield 7b, barrel 7c and inner plunger stopper 7d. A plunger rod 8 is arranged axially in the cylinder 7c. The end of plunger rod is configured for engaging with the plunger stopper 7d following an axial sliding to push it forward when the drug is dispensed. The other end of the piston rod 8 extends axially as a tubular housing 9 to retain a plunger spring 10 therein. With reference also to FIGS. 4 and 5, the tubular housing 9 extends within the dose selection knob 4 and the plunger spring 10 winds around a boss 4a extending from a bottom face 4b of the knob 4, against which the plunger spring 10 abuts. The arrangement of the plunger spring 10 between the inner wall of the tubular housing 9 and the boss 4a of the knob 4 helps to minimize buckling of the spring, which at the beginning in a compressed state between the bottom face 4b of the knob 4 and the bottom of the housing 9.

Figure 7:
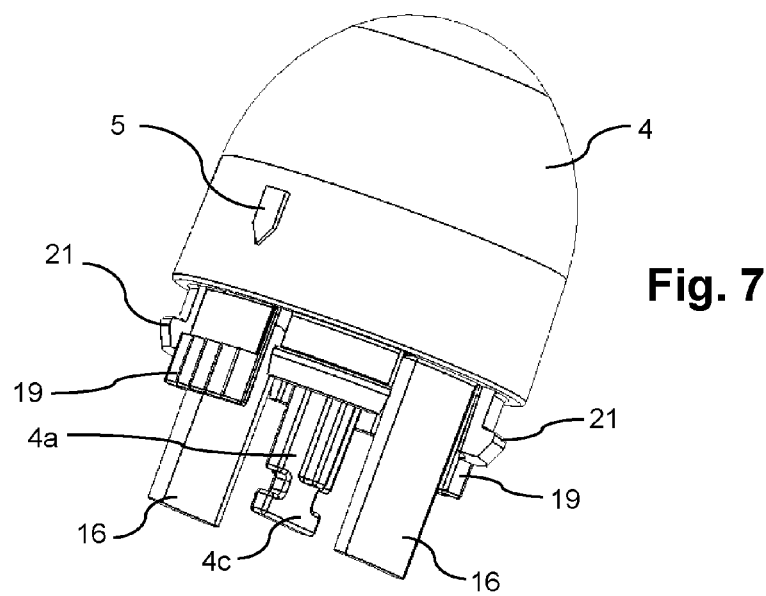
FIG. 7 is a perspective view of the dose selection knob of the device of FIG. 1.
Figure 8:
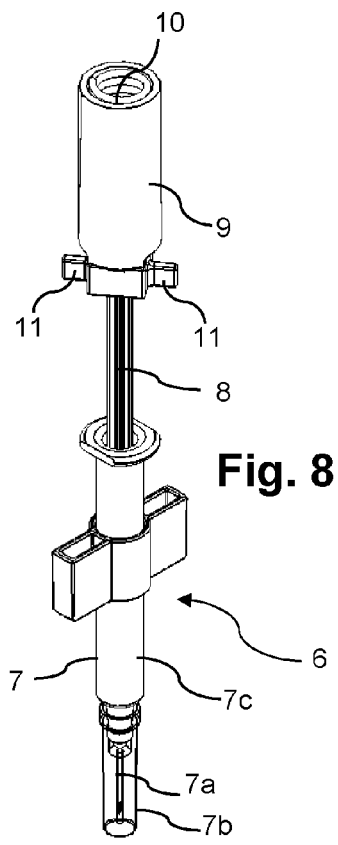
FIG. 8 is an axial section of the dose selection knob of FIG. 7.
Figure 9:
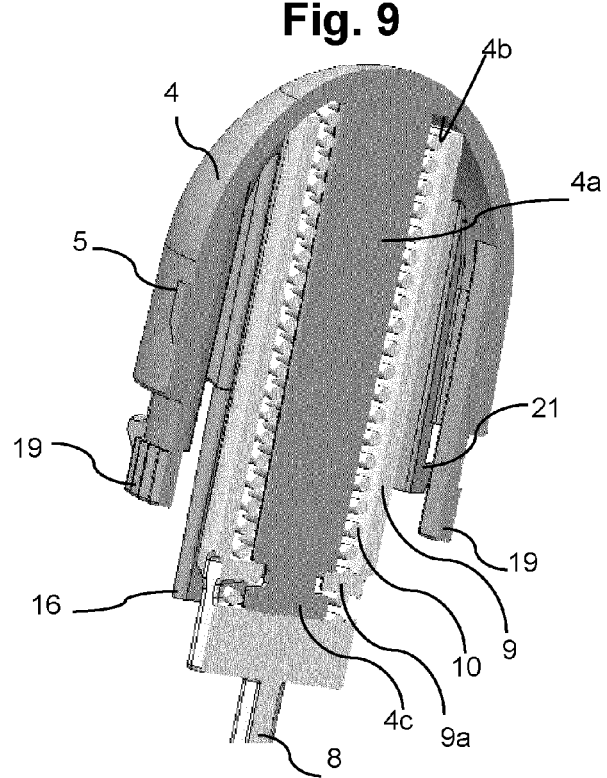
FIG. 9 is an overall view of the syringe unit inside the device of FIG. 1.

As also shown in greater detail in FIGS. 7 and 9, the boss 4a is connected to the tubular housing through a bayonet connection formed by a substantially T-shaped end 4c of the boss 4a and two diametrically opposed, inner abutments 9a of the tubular housing 9. When the arrow 5 of the knob 4 is aligned to the reference mark 0 of the collar 3, the two abutments 9a engage with the T-shaped end 4c at opposite sides thereof, biased against said end by the spring 10. As a result of an axial angular displacement of the knob 4 the T-shaped end disengages from the abutments 9a and the tubular housing 9, and consequently the plunger rod 8, is made free to slide axially under the action of the spring 10.

Two radial pegs 11 are formed at the end of the tubular housing 9, from which the plunger rod 8 extends, outwardly projecting from diametrically opposed parts. The two pegs 11 are designed to slide in a guide channel to drive the movement of the piston rod 8 controlling the drug delivery, as explained later on.

Figure 10:
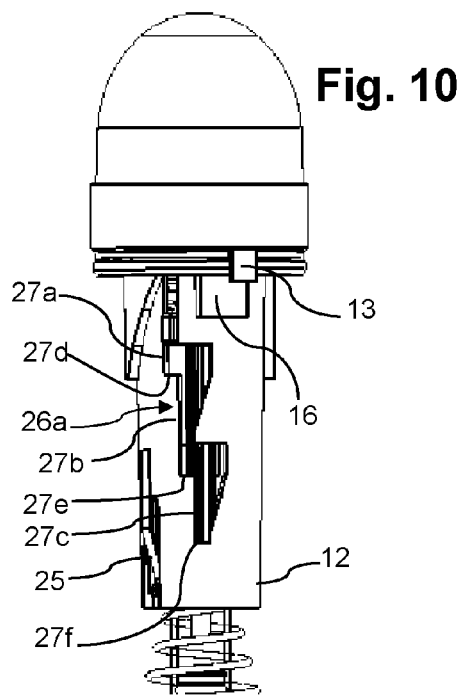
FIG. 10 shows the selection knob mounted on the plunger rod.
Figure 11:
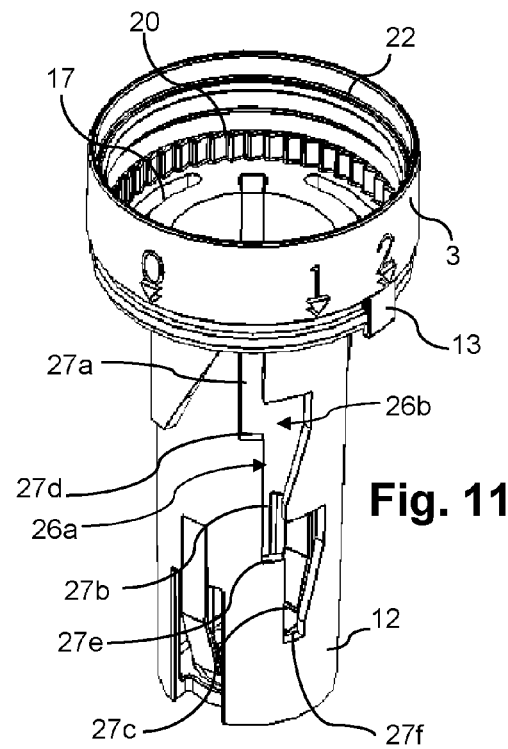
FIG. 11 shows the plunger rod in an upward perspective view.
Figure 12:
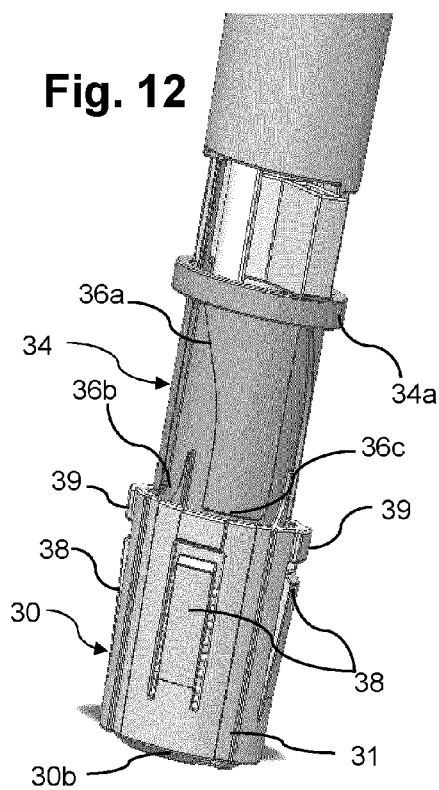
FIG. 12 shows the front portion of the device, parts being removed for sake of clarity.

The collar 3 constitutes the enlarged end of a plunger sleeve 12, shown in particular in FIGS. 10 and 11, coaxial to the plunger rod 8 and integral to the outer body 1 through an alignment tooth 13 engaging with a corresponding perimetrical slot 14 formed on the inner wall of the outer body 1. The dose selection knob 4 is integral to a dose selection sleeve 15, coaxial to the outer body 1, through a pair of diametrically opposed, axial legs 16 which, by passing through grooves 17 of the plunger sleeve 12, engage with corresponding recesses 18 formed on the edge of the selection sleeve 15. The selection knob 4 is connected to the plunger sleeve 12 in a rotatable, unidirectional fashion through a pair of diametrically opposed, axial toothed legs 19 engaging with a ratchet ring 20 formed on the inner face of the collar 3 and through a pair of retention clips 21 slidingly engaging in a corresponding annular groove 22 also formed on the inner face of the collar 3. The ratchet ring 20 has a profile that allows the angular displacement of the knob 4 to occur in only one direction, whereby the user cannot bring the knob back to a previous state.

A transfer sleeve 23 is coaxially arranged between the plunger sleeve 12 and the dose selection sleeve 15. The transfer sleeve 23 controls the movement of the plunger rod 8 to trigger a dose delivery, as will be described later on.

As shown in FIG. 4, the plunger sleeve 12 is connected to the syringe 7 through an end flange of the barrel 7c resting on a flange 24 inwardly projecting at the free end of the plunger sleeve 12. To prevent reverse motion of the syringe, the flange of the barrel 7c is locked against the flange 24 by two syringe retention clips 25 inwardly bent from the side wall of the plunger sleeve 12. The clips 25 flex outwardly to allow the syringe unit 6 to be inserted into the plunger sleeve 12 and then elastically flex back to the syringe locking position.

On the side surface of the plunger sleeve 12 there are formed guide means for dose pegs 11 comprising two guide channels 26a, 26b longitudinally extending at diametrically opposed parts and symmetrical to the axial rotation as regards their shape. As shown in FIGS. 10 and 11, each channel is formed with a step profiled edge: each profile has a first, second and third linear length 27a, 27b, 27c, in particular parallel to the axis X, separated by two ledges 27d, 27e, the first linear length 27a starting from the inner base of the collar 3, the third linear length 27c ending with an abutment land 27f.

Figure 6:
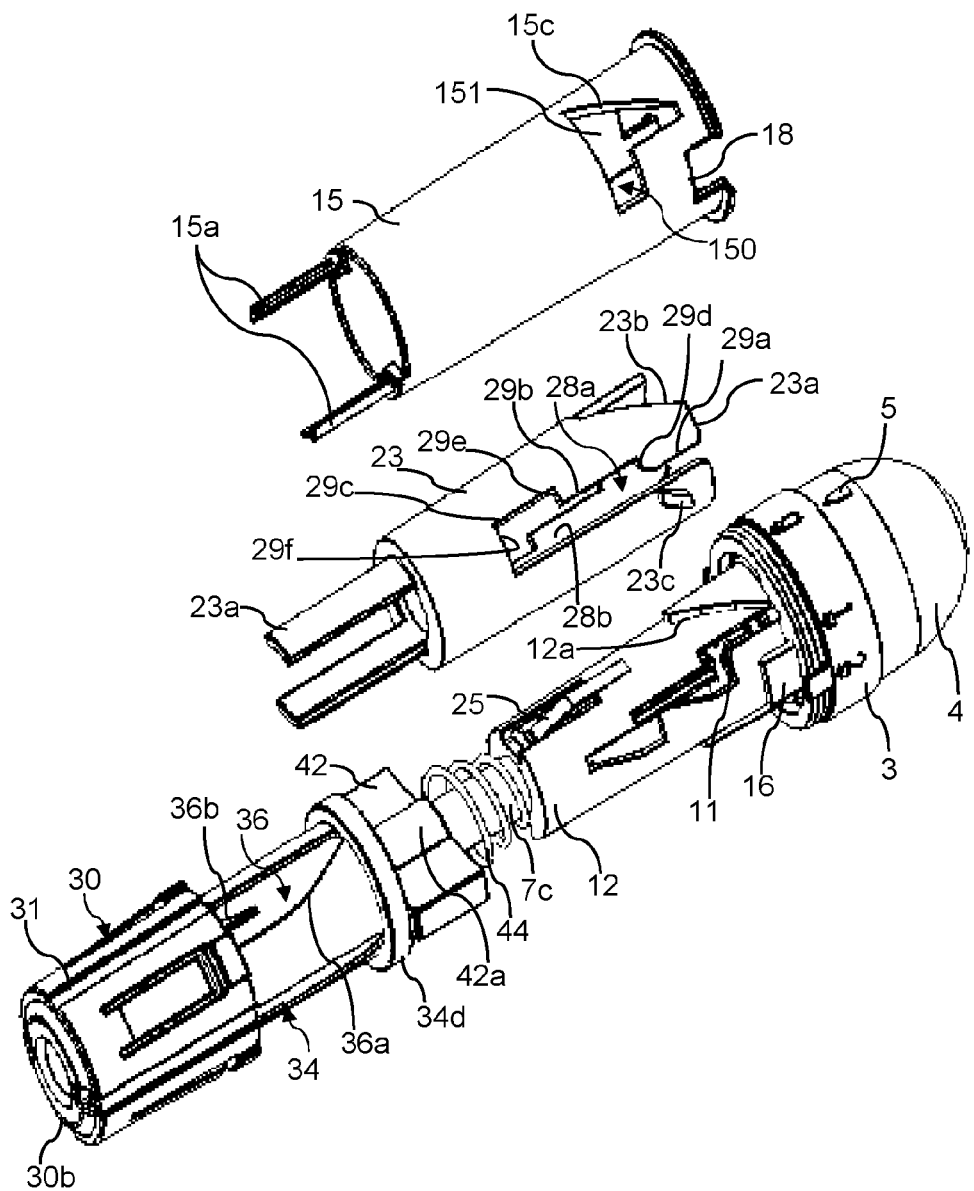
FIG. 6 is an enlarged exploded view of the device of FIG. 1, some parts being removed for sake of clarity.

As shown in FIG. 6, on the side surface of the transfer sleeve 23 there are formed cam means for driving dose pegs 11 comprising two cam channels 28a, 28b longitudinally extending at diametrically opposed parts and symmetrical to the axial rotation as regards their shape. Each channel is formed with a step profiled edge having a reverse profile to the step profiled edge of the guide channels 26a and 26b: each profile has a first, second and third linear length 29a, 29b, 29c, in particular parallel to the axis X, separated by two steps 29d, 29e, the first linear length 29a starting from an edge 23a of the transfer sleeve 23, the third linear length 29c ending with an abutment land 29f.

The plunger sleeve 12 and the transfer sleeve 23 are mounted in a way that, when the device is triggered for dose delivery, the two guide channels 26a, 26b and the two cam channels 28a, 28b are substantially aligned on a diametrical plane containing the axis X.

As shown again in FIG. 6, the transfer sleeve 23 has also a pair of diametrically opposed, first dose trigger cams 23b and a pair of diametrically opposed, second dose trigger cams 23c, for interacting, at successive times, with corresponding guide track surfaces 12a on the plunger sleeve 12 and, respectively, corresponding guide track surfaces 15c on the plunger sleeve 15, as explained later. On the selector sleeve 15 there is formed a pair of diametrically opposed openings 150 with two circumferential sides in which the pair of second dose trigger cams 23c slidingly engages. The pair of openings 150 leads to a respective pair of openings 151 of substantially triangular shape, with a side extending on one of the sides of the opening 150, while the other one, opposite to the opening 150, is the guide track surface 15c.

As shown in FIGS. 4, 6, 12 and 13, a slide 30 is axially mounted at the front end of the outer body 1. The slide 30 slides within the outer body 1 through a linear joint formed by longitudinal splines 31 formed on the outer surface of the slide 30 and corresponding rims 32 formed in the outer body 1, and engaging with each other. A tubular boss 33, in which the needle 7a is positioned with the relevant needle shield 7b of the syringe 7, extends axially in the slide 30. The boss 33 extends from a bottom wall 30a of the slide 30, whose outer face, or front face, indicated at 30b is designed to come into contact with the patient at the point of the injection.

Figure 13:
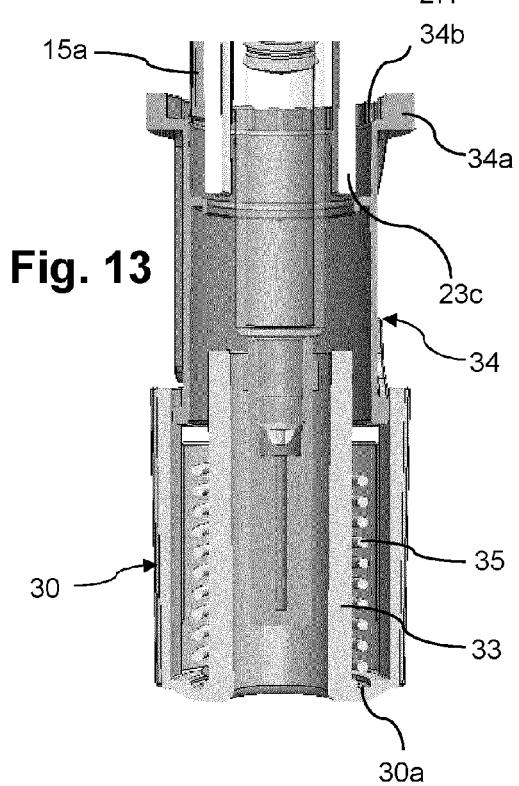
FIG. 13 is an axial section of the front portion of FIG. 12.
Figure 14:
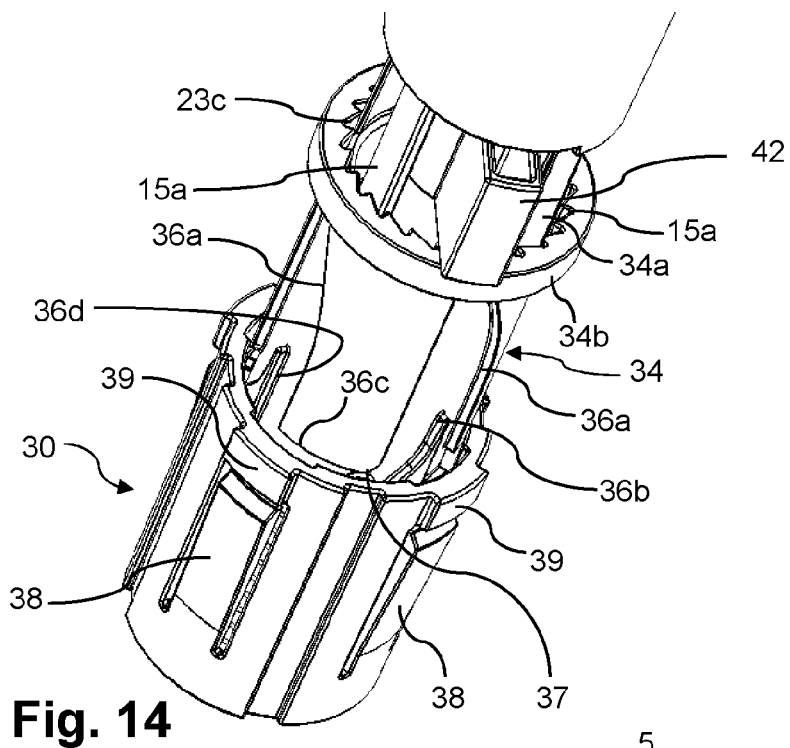
FIG. 14 is an upward perspective view of the front portion of FIG. 12.

At the opposite side of the bottom wall 30a, the slide 30 is connected to a cam ratchet 34 that serves as a way to unlock the device ready for injection and then lock it again upon retraction after the injection, via a series of cam tracks. The selector sleeve 15 interacts with the cam ratchet 34, as shown in FIGS. 13 and 14. In particular, two toothed end legs 15a extend from the selection sleeve 15 and engage with a ratchet ring 34a formed on the inner face of an end flange 34b of the cam ratchet 34. The teeth are configured for allowing an angular displacement in one direction only. The transfer sleeve 23 in turn has two arms 23c whose free ends abuts on the tubular boss 33 of the slide 30 when the latter is depressed. A return spring 35 is arranged in the slide 30 around its boss 33 and abuts on the bottom wall 30a and against the end of the cam ratchet 34 engaged within the slide 30.

A cam track 36 is embossed on the outer surface of the cam ratchet 34. The cam track 36 is repeated four times in an angularly equiispaced fashion on said surface and is divided into two portions of cam track, for sake of simplicity called upward portion 36a, extending for an end of the cam ratchet 34 and inclined with respect to axis X, and downward portion 36b, extending from the same end of cam ratchet 34 and incident with the upward portion 36a. A pair of diametrically opposed lock-out pegs 37 inwardly projecting in the slide 30 are designed to slide on said cam tracks 36. In the rest state of the device the lock-out pegs 37 abut on a lock-out edge 36c (FIGS. 4 and 14) extending circumferentially between the end of a cam track downward portion 36b and the beginning of the angularly adjacent cam track upward portion 36a. The descendant cam track 36b also defines an abutment 36d serving as end stroke for the lock-out pegs 37.

Four equispaced flexible tines 38 project from the side outer surface of the slide 30 and the end edge of the outer body 1 abuts against them. The tines 38 have an inclined face contacting said edge in such a way to allow the edge to slide on said face, as a result of which the tine flex inwardly letting the slide 30 slide relative to the outer body 1. To control the axial sliding of the slide 30 endstop pins 39 running in corresponding tracks 40 of the outer body 1 are formed on the edge of the cursor 30 aligned to the flexible tines 38. Furthermore the endstop pins 39 serve as endstroke for the slide 30 to prevent the slide 30 from escaping out of the front of the device, by abutting on a corresponding endstop rim 41 formed along the front edge of the outer body 1.

A window body 42 is placed between the edge of the end flange 34b of the cam ratchet 34 and the front end of the transfer sleeve 23 and has a central tubular housing 42a placed between the legs of the transfer sleeve 23 for sitting the barrel 7c of the syringe 7. The window body 42 in made of transparent material and fits into a window aperture 43 of the outer body 1, whereby the user can check the drug for any degradation prior to use or a device state change (no dose delivered, first dose delivered, second dose delivered).

A spring 44 is provided around the barrel 7c of the syringe 7 to axially separate the plunger sleeve 12 and the transfer sleeve 23. Due to the different diameters of these components, the spring 44 is conical in shape.

A needle shield remover 45 of the needle shield 7b is removably fixed to the outer body 1 by snap retention pins 45a and has an inner tubular boss 45b engaging with the needle shield 7b, whereby, pulling the remover 45 before the first dose delivery, the user can remove the needle shield 7b to expose the needle 7a ready for dose delivery.

The following is a description of the way the auto-injector device according to the invention may be used.

Figure 15:
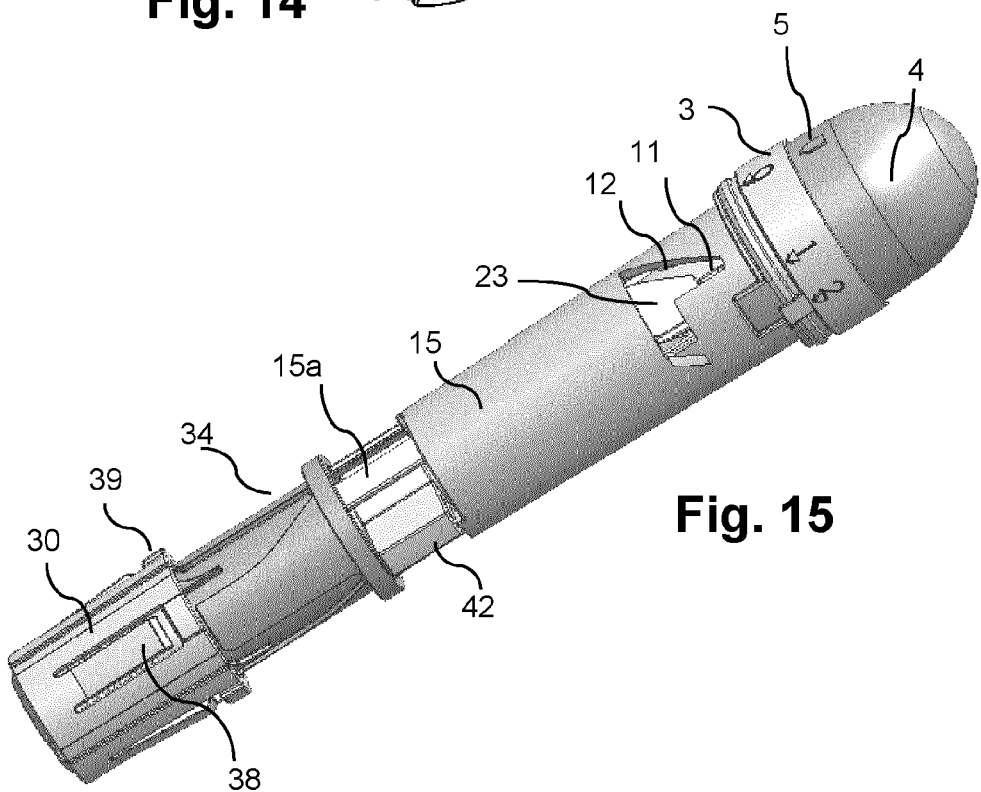
FIG. 15 shows the device in its stored state.

In the initial state, the stored state (FIG. 15) the drive spring 10 is fully compressed between the rear surface 4b of the dose selection knob 4 and the inside bottom surface of its tubular housing 9. The bayonet connection between the knob 4 and the housing 9 secures the drive spring 10 in compression until the first dose is selected. The needle shield 7b is secured to the syringe 7 and the needle shield remover 45 secured to the needle shield 7b. The cap 2 is secured to the outer body 1 and the slide 30 is prevented from moving axially because the lock-out pegs 37 of the slide 30 abut against the lock-out edge 36c of the cam ratchet 34.

The plunger sleeve 12 is connected to the outer body 1 in a way that it cannot move rotationally or axially relative to the outer body 1 once assembled. The dose selection knob 4 is connected to the plunger sleeve 12 in a way that it can only rotate in one direction relative thereto. The direction of rotation is indicated by the numbering on the collar 3; i.e. the arrow on the dose selection knob starts at 0, rotates to 1 when dose 1 is selected, then rotates to 2 when dose 2 is selected.

First the user must slide back and remove the cap 2 from the device in order to expose the needle shield remover 45. The user shall replace the cap 2 once the first dose is delivered when the device is not in use. The cap 2 protects the drug from light exposure and prevents particulates from coming into contact with the front face of the device.

To perform the first injection the user must remove the needle shield remover 45, taking the needle shield 7b with it and leaving the needle 7a uncovered, which however remains sub-flush of the front face of the slide 30. To unlock and arm the triggering mechanism for the delivery of the first dose, the user simply rotates the dose selection knob 4 from position 0 (rest state) to position 1 (first dose armed state).

Figure 16:
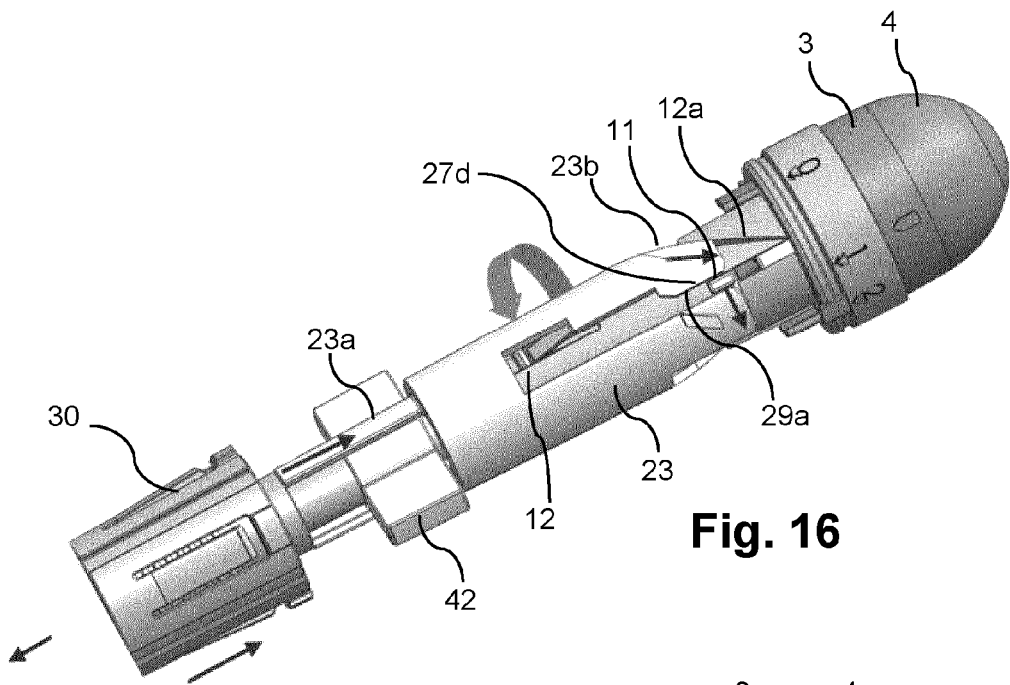
FIG. 16 shows the first dose armed device and ready for triggering.

Rotating the dose selection knob 4 causes the initialization of the plunger spring 10 through the unlocking of the bayonet connection 4c, 9a between the spring boss 4a of the knob 4 and the tubular housing 9 of the plunger rod 8 unlocking the drive spring 10. Unlocking the drive spring 10 causes an initial sliding of the plunger rod 8 and the two radial pegs 11, aligned in the respective channel guides 26a, 26b of the plunger sleeve 12, slide along them to be driven onto the first ledge 27d between the first linear length 27a and the second linear length 27b (FIG. 16). At this stage the radial pegs 11 axially slide without any angular movements, but are secured from rotating as the plunger sleeve 12 is integral to the outer body 1 and they rest on the step 27d until device is triggered.

Rotation of dose selection knob 4 also causes the rotation in the same direction of the selection sleeve 15 integral thereto and of the cam ratchet 34 through the arms 15a with their toothed ends engaged within the ratchet ring 34a of the cam ratchet 34. The rotation of the cam ratchet 34 causes the relative sliding of the lock-out pins 37 of the slide 30 on the abutment edge 36c of the cam ratchet 34 until the pins 37 are driven at the inlet of the upward portion 36a of the cam track 36 formed on the lateral surface of the cam ratchet 34. It has to be noted that dose selection knob 4 cannot be rotated beyond the position 1 until the slide 30 has been depressed for first dose due to the wall 36d limiting the sliding of the lock-out pins 37 along the abutment edge 36c.

To trigger the device the user presses the front surface of the slide 30 against the injection site by keeping the device by means of its outer body 1. Depressing the slide 30 causes a force resistance due to the contrast between the flexible tines 38 of the slide 30 and the end of the outer body 1. Thanks to their flexibility and the inclined contact surface the flexible tines 38 yield to the pressure and deflect inwardly to allow full axial depression of the slide 30 in the outer body 1 letting the needle 7a protrude into the injection site. The movement subsequently generated by the release of the flexible tines 38 quickly inserts the needle 7a into the injection site.

The axial sliding of the slide 30 as a result of the pressure exerted by the user on the injection site causes the cam ratchet 34 to axially rotate in the direction opposite to that of the inclination of the upward portion 36a of the cam track 36, because the lock-out pegs 37 slide against it. The slide 30 is prevented from rotating due to the connection with the outer body via linear joint 31, 32. During this movement, the ratchet ring 34a of the cam ratchet 34 rotates in the allowed direction in view of the fact the dose selection sleeve 15, engaged with its toothed ends of its arms 15a in the ratchet ring 34a, is prevented from rotating as it is linked to the dose selection knob 4 via the interface formed by the dose selection feet 16 of the knob 4 engaged in the recesses 18 of the dose selection sleeve 15. Unidirectional rotation of the dose selection knob 4 is achieved via the interface between the ratchet teeth 20 on the plunger sleeve 12 and the corresponding ratchet teeth 19 on the dose selection knob 4. The teeth of this interface are so designed as to oppose more resistance to rotation than that between cam ratchet 34 and the selection sleeve 15. Therefore the dose selection sleeve 15 remains stationary and the cam ratchet 34 ratchets over the toothed feet of the dose selection sleeve until the slide 30 reaches the end stroke of its axial slide.

Figure 17:
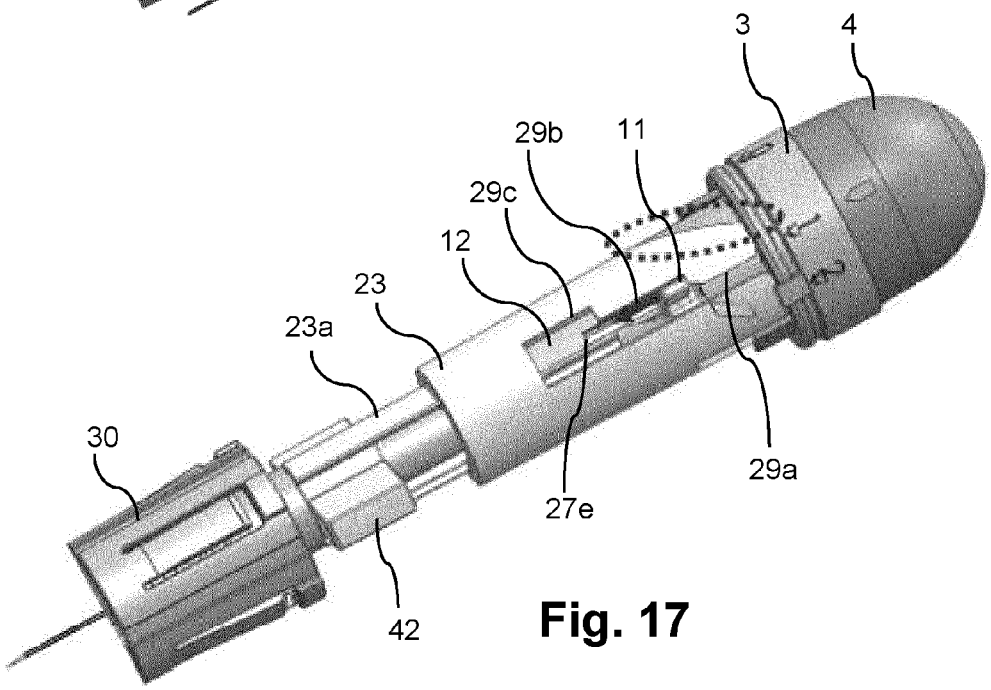
FIG. 17 shows the device at the beginning of the first dose delivery step.

Once the flexible tines 38 of the slide 30 deflect sufficiently to allow the slide 30 to move axially inside the outer body 1, the tubular boss 33 on the slide 30 contacts the trigger legs 23a of the transfer sleeve 23. This in turn pushes the transfer sleeve 23 towards the rear of the device. During its axial movement (FIG. 16) the first dose trigger cam 23b on the transfer sleeve 23 interacts with the first dose cam track surface 12a on the plunger sleeve 12, thereby rotating the transfer sleeve 23. As the transfer sleeve 23 rotates, the dose pegs 11 on the plunger rod 8 are moved on the first ledge 27d of the guide channel 26a, 26b by the first linear length 29a of the cam channel 28a, 28b of the transfer sleeve 23 up to its end from which they fall off on the second ledge 27e. The diametrical alignment of the cam channel 28a, 28b and the guide channel 26a, 26b allows the axial sliding of the dose pegs 11 under the action of the drive spring 10, as shown in FIG. 17, this resulting in the sliding of the plunger rod 8 and in the first dose delivery.

Figure 18:
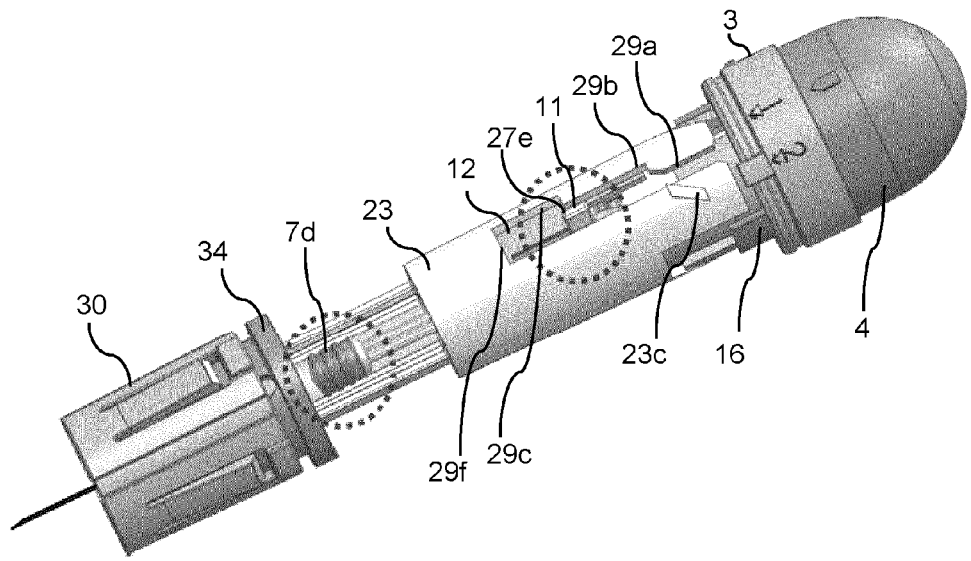
FIG. 18 shows the device at the end of the first dose delivery step.

The first dose delivery occurs because the plunger stopper 7d in the syringe 7 is propelled forward by the plunger rod 8 which in turn is caused to slide by the drive spring 10 and ends when the dose pegs 11 reach the second ledge 27e of the guide channel 26a, 26b on the plunger sleeve 12 (FIG. 18). The separation spring 44 remains compressed between the transfer sleeve 23 and the plunger sleeve 12 during the delivery of the first dose.

Figure 19:
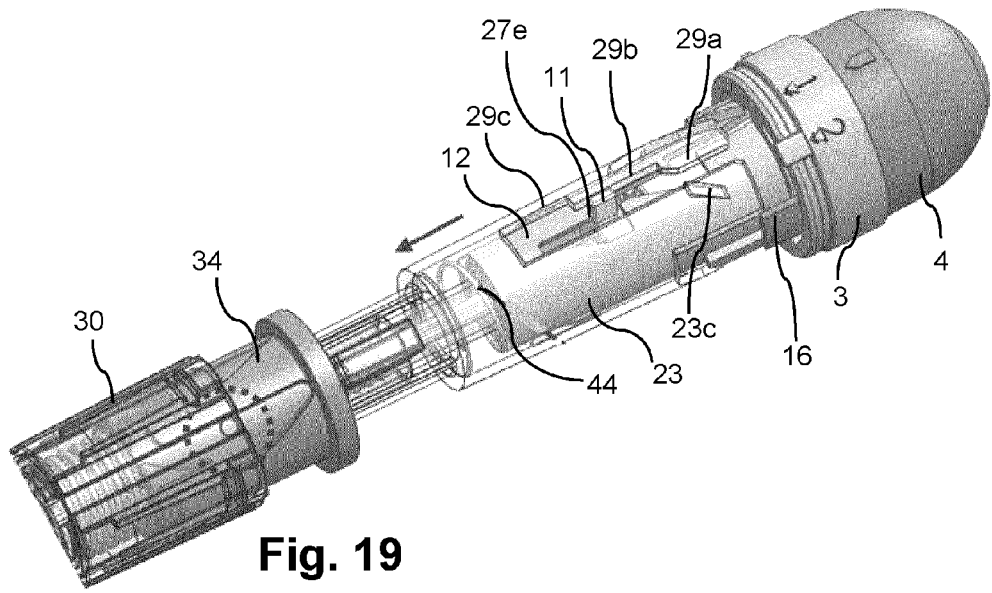
FIG. 19 shows the device at the reset step between the delivery of the first and the second dose.

Once the first dose is delivered, the user removes the device from the injection site after the prescribed waiting period. In this way the automatic needle protection and trigger mechanism reset. The return spring 35 is no more hindered by the forced contact between the device front surface and the injection site and therefore pushes the slide 30 axially forward (FIG. 19), while the separation spring 44 decompresses to push transfer sleeve 23 in the same direction moving it away from the plunger rod 8 to reset the trigger mechanism. Lock-out pins 37 on slide 30 interact with the downward portion 36b of the cam 36 by rotating the cam ratchet 34. The slide 30 is prevented from rotating due to the longitudinal ribs 32 engaged with the splines 31 on the outer body 1.

Figure 20:
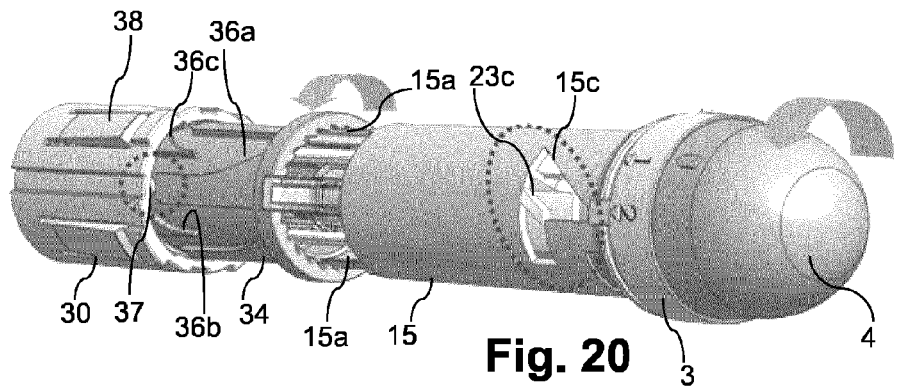
FIG. 20 shows the device at the time when it is armed for the second dose.

As the cam ratchet 34 rotates, it also ratchets over the toothed legs 15a of the dose selection collar 15. The dose selection collar 15 and dose selection knob 4 do not rotate due to the resistance provided by the ratchet teeth on the plunger sleeve 12 and the corresponding ratchet teeth on the dose selection knob 4. Once the return spring 35 has returned the slide 30 to its fully extended position (FIG. 20), the lock-out pins 37 on the slide 30 and the lock face of the cam ratchet 34 prevent the slide 30 from being depressed (as the cam ratchet 34 is prevented from moving axially toward the rear of the device by the window 42).

The needle 7a is now prevented from being accessed since it is covered by the slide 30. The slide 30 cannot be depressed again until the position 2 is selected by the user by means of rotation of the dose selection knob 4. Then the user recaps the device.

If the delivery of a second dose is required, the user removes the cap 2 and rotates the knob 4 from position 1 (first dose armed position) to position 2 (second dose armed position) to unlock the device.

Figure 21:
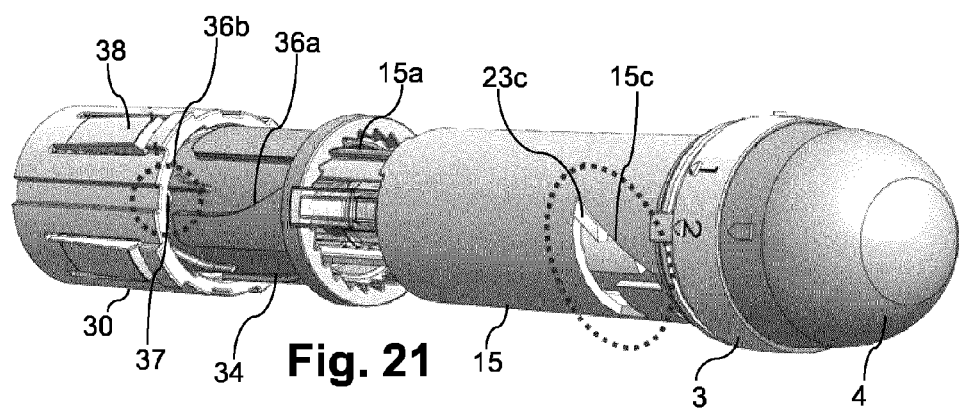
FIGS. 21 and 22 show the device armed for the second dose delivery at two different views.
Figure 22:
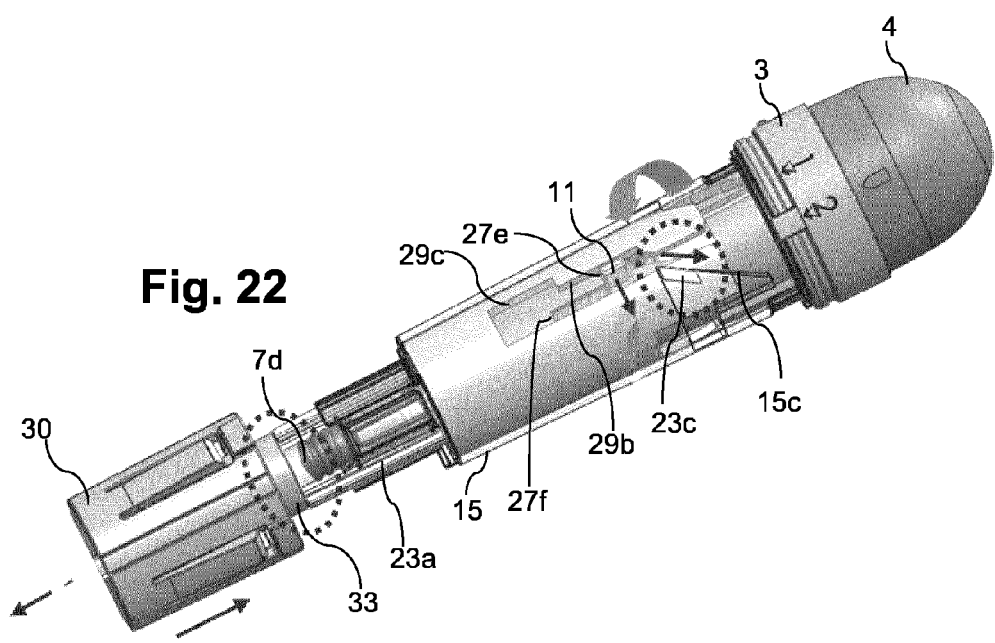

With reference to FIGS. 21 and 22, rotation of dose selection knob 4 causes the rotation in the same direction of the selection sleeve 15 integral thereto, thus aligning the second dose trigger cam 23c on the transfer sleeve 23 and the second dose cam track surface 15c on the selector sleeve 15, and the rotation of the cam ratchet 34 through the arms 15a with their toothed ends engaged within the ratchet ring 34a of the cam ratchet 34 to unlock the slide 30. The rotation of the cam ratchet 34 causes the relative sliding of the lock-out pins 37 of the slide 30 on the abutment edge 36c of the cam ratchet 34 until the pins 37 are driven at the inlet of the upward portion 36a of the cam track 36 formed on the lateral surface of the cam ratchet 34. It has to be noted that dose selection knob 4 cannot be rotated past position 2 due to lock-out pins 37 whose sliding along the abutment edge 36c is limited by the wall 36d.

To trigger the device the user presses the front surface of the slide 30 against the injection site by keeping the device by its outer body 1. Depressing the slide 30 causes a force resistance due to the contrast between the flexible tines 38 of the slide 30 and the end of the outer body 1. Thanks to their flexibility and the inclined contact surface the flexible tines 38 yield to the pressure and deflect inwardly to allow full axial depression of the slide 30 in the outer body 1 letting the needle 7a protrude into the injection site. The motion subsequently created by the release of the tines quickly inserts the needle 7a into the injection site.

The axial sliding of the slide 30 as a result of the pressure exerted by the user on the injection site causes the cam ratchet 34 to axially rotate, because the lock-out pegs 37 slide against the upward portion 36a of the cam track 36. The slide 30 is prevented from rotating due to the connection with the outer body via linear joint 31, 32. During this movement, the ratchet ring 34a of the cam ratchet 34 rotates in the allowed direction in view of the fact the dose selection sleeve 15, engaged with its toothed ends of its arms 15a in the ratchet ring 34a, is prevented from rotating as it is linked to the dose selection knob 4 via the interface formed by the dose selection feet 16 of the knob 4 engaged in the recesses 18 of the dose selection sleeve 15. Unidirectional rotation of the dose selection knob 4 is achieved via the interface between the ratchet teeth 20 on the plunger sleeve 12 and the corresponding ratchet teeth 19 on the dose selection knob 4. The teeth of this interface are so designed as to oppose more resistance to rotation than that between cam ratchet 34 and the selection sleeve 15. Therefore the dose selection sleeve 15 remains stationary and the cam ratchet 34 ratchets over the toothed feet of the dose selection sleeve until the slide 30 reaches the end stroke of its axial slide.

Figure 23:
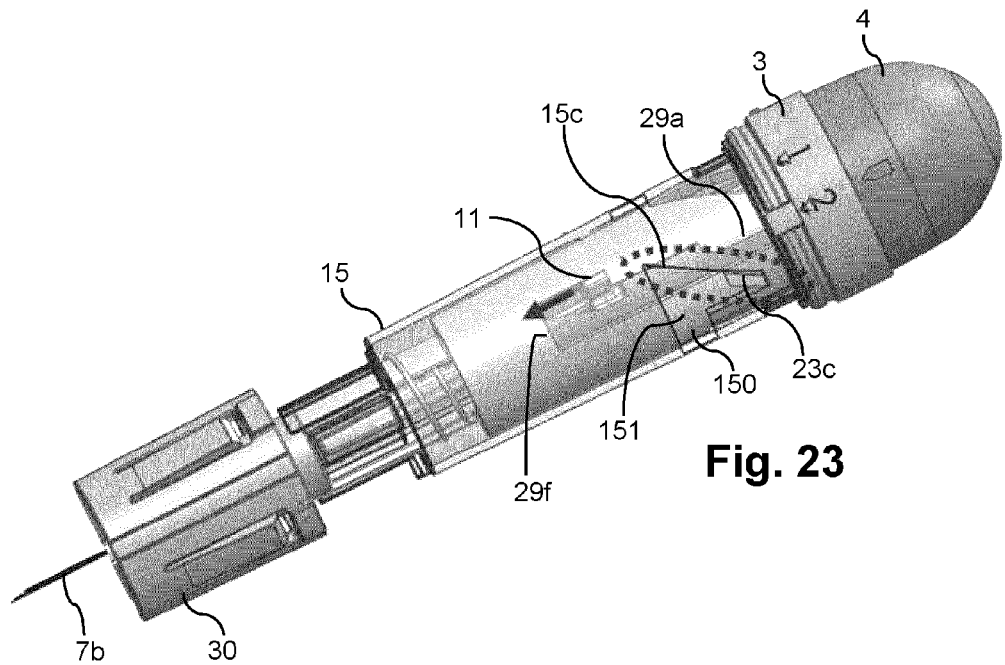
FIG. 23 shows the device at the beginning of the second dose delivery step.
Figure 24:
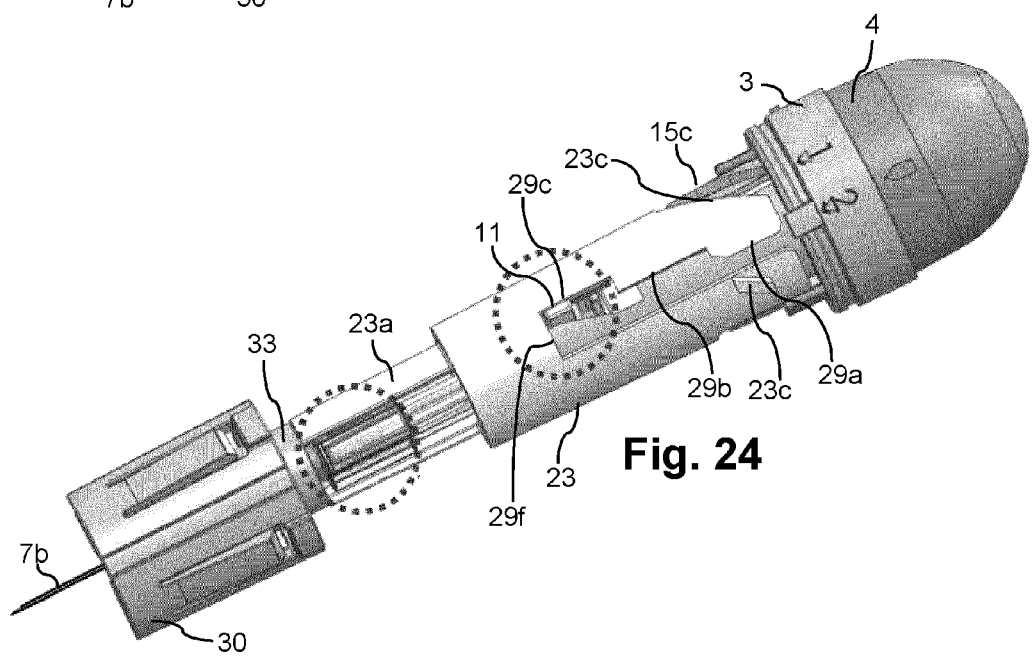
FIG. 24 shows the device at the end of the second dose delivery step.

Once the flexible tines 38 of the slide 30 deflect sufficiently to allow the slide 30 to move axially inside the outer body 1, the tubular boss 33 on the slide 30 contacts the trigger legs 23a of the transfer sleeve 23. This in turn pushes the transfer sleeve 23 towards the rear of the device. During its axial movement (FIGS. 23 and 24) the second dose trigger cam 23c on the transfer sleeve 23 interacts with the second dose cam track surface 15c on the selection sleeve 15, thereby rotating the transfer sleeve 23. As the transfer sleeve 23 rotates, the dose pegs 11 on the plunger rod 8 are shifted off the second ledge 27e of the guide channel 26a, 26b by the second linear length 29a of the cam channel 28a, 28b of the transfer sleeve 23. The diametrical alignment of the cam channel 28a, 28b and the guide channel 26a, 26b allows the fall off of the dose pegs 11 from the second ledge 27e to the third ledge 27f and their axial sliding under the action of the drive spring 10, this resulting in the sliding of the plunger rod 8 and the second dose delivery.

The second dose delivery occurs because the plunger stopper 7d in the syringe 7 is propelled forward by the plunger rod 8 which in turn is caused to slide by the drive spring 10 and ends when the dose pegs 11 reach the third ledge 27f of the guide channel 26a, 26b on the plunger sleeve 12. The spring 44 remains compressed between the transfer sleeve 23 and the plunger sleeve 12 during delivery of the second dose.

It is worth noting that a small volume of the drug always remains in the barrel 7c of the syringe 7. In fact, the position of the third ledge 27f of the guide channel 26a, 26b is designed in the way that, when the radial pegs 11 reach the third ledge 27f, the plunger stopper 7d does not touch the bottom of the barrel 7c. In this way, not only the delivery of the prescribed volume of drug is allowed to be controlled, but also any manufacturing variability with respect to the internal length of the syringe barrel 7c is ensured to be mitigated. Therefore the dose accuracy is improved.

Once the second dose is delivered, the user removes the device from injection site after the prescribed waiting period. The return spring 35 is not hindered by the forced contact between the device front surface and the injection site and therefore pushes the slide 30 axially forward, while the spring 4 decompresses to push transfer sleeve 23 in the same direction moving it away from the plunger rod 8. Lock-out pins 37 on the slide 30 interact with the downward portion 36b of the cam 36 by rotating the cam ratchet 34. The slide 30 is prevented from rotating due to the longitudinal ribs 32 engaged with the splines 31 on the outer body 1.

As the cam ratchet 34 rotates it also ratchets over the toothed legs 15a of the dose selection collar 15. The dose selection collar 15 and dose selection knob 4 do not rotate due to the resistance provided by the ratchet teeth on the plunger sleeve 12 and the corresponding ratchet teeth on the dose selection knob 4. Once the return spring 35 has returned the slide 30 to its fully extended position, the lock-out pins 37 on the slide 30 and the lock face of the cam ratchet 34 prevent the slide 30 from being depressed (as the cam ratchet 34 is prevented from moving axially toward the rear of the device by the window 42).

The needle 7a is again prevented from being accessed due to being covered by the slide 30, which cannot be depressed further and the device is spent. Then the user recaps the device before disposal/handling to paramedic.

Even if the autoinjector device according to the invention described above is equipped with two dose pegs 11 to guide the movements of the plunger rod 8, this solution being the preferred one to have a symmetrical distribution of the forces acting on the various components, it is clear that the solution in which only one dose peg 11 is provided is comprised in the scope of the invention as being an obvious variation thereof. In this case, the stepped guide means 44 and the cam means for driving and triggering the device will be modified consequently.

The autoinjector device according to the invention is suitable to the delivery of medicaments in solution, especially epinephrine (also known as adrenaline).

In particular, the doses of epinephrine that can be administered with the device of the invention are preferably in the range of 0.05 mg to 0.5 mg for each delivered dose (from 0.1 mg to 1 mg if two doses are considered).

Preferred doses for each delivery are 0.05 mg, 0.10 mg, 0.15 mg, 0.30 mg and 0.50 mg.

The above said doses are based on a concentration of the epinephrine solution preferably ranging from 0.05 mg/ml to 0.5 mg/ml, the concentrations 0.05 mg/ml, 0.1 mg/ml, 0.16 mg/ml, 0.3 mg/ml and 0.5 mg/ml being particularly preferred.

The invention claimed is:

1. An automatic medicament injection device comprising: an outer body extending along a longitudinal axis;
a syringe unit arranged in said outer body and fixed therewith, comprising a syringe containing a medicament to be injected, a needle and piston means slidable axially;
means for arming the device from a rest position to a first armed position for delivering a first dose and to a second armed position for delivering a second dose, said means for arming being arranged at one end of said outer body and comprising a dose selection sleeve extending within said outer body;
first elastic means arranged between said means for arming and said piston means, said first elastic means being in a compressed state when the device is in its rest position and decompressing to push forward said piston means and deliver said first and said second dose one after the other;
an inner body secured to said outer body and coaxial thereto, said piston means being slidably arranged therein,
guide means between said inner body and said piston means for controlling the axial sliding motion of said piston means relative to said inner body, said guide means comprising first guide members formed on said inner body and second guide members extending from said piston means and slidingly engaging within said first guide members;
a slide arranged at the other end of said outer body and constrained to slide axially therewith as a result of a pressure exerted on its free end against a second elastic means arranged between said slide and said outer body between a first position, wherein the sliding motion of the slide is prevented and the slide extends from said outer body over the syringe needle, and a second position, wherein said slide is retracted in said outer body exposing the syringe needle;
cam transmission means between said slide and said inner body to transform the axial sliding of the slide into a triggering command for the device, comprising a transfer sleeve sliding as a result of the sliding of the slide and being formed with first cam means of the transfer sleeve for interacting with said second guide members of piston means, said transfer sleeve being axially pivotable as a result of interaction of second cam means of the transfer sleeve with said inner body and said selection sleeve, whereby said transfer sleeve is subjected to a first and a second angular displacement which, through said first cam means, displaces said second guide members pushing them to a first dose triggering condition and afterwards, to a second dose triggering condition; and
third cam means being provided arranged within said outer body and pivotable in only one direction as a result of the axial sliding of said slide, said third cam means defining a cam track configured for controlling the motion of the slide from said first position to said second position and back to said first position controlled by said second elastic means once said pressure exerted on the free end of said slide ceases.

2. The device according to claim 1, wherein said first guide members comprise two guide channels longitudinally extending at diametrically opposed parts and symmetrical to an axial rotation as regards to their shape, each channel being formed with an edge profiled with ledges separated by linear lengths ending with an abutment land, said second guide members comprising a pair of radial pegs extending at diametrically opposite sides and engaging in said guide channels, in said first and second armed position said pegs resting on said ledges.

3. The device according to claim 2, wherein said transfer sleeve of said cam transmission means is coaxial to said inner body and is arranged slidably and pivotally thereon and said first cam means comprise two cam channels longitudinally extending at diametrically opposed parts and symmetrical to the axial rotation as regards to their shape, each of said channels being formed with an edge profiled with steps separated by linear lengths and ending with an abutment land, said stepped profile having a reverse profile to the step profiled edge of said guide channels, said linear lengths abutting against said pegs at said first and second armed position to push them in said guide channels from said steps, causing the device to trigger for delivering the first dose and, afterwards, the second dose.

4. The device according to claim 1, wherein said second cam means comprise a pair of diametrically opposed, first dose trigger cams and a pair of diametrically opposed, second dose trigger cams for interacting, at successive times, with corresponding guide tracks on said inner body and, respectively, with corresponding guide tracks on said selection sleeve.

5. The device according to claim 4, wherein on said selection sleeve there is formed a first pair of diametrically opposed openings having two sides extending circumferentially, said pair of second dose trigger cams engaging in said openings, the first pair of openings widening in a second pair of respective openings of a substantially triangular shape, a side of which being aligned with one of the sides of the opening of said first pair, while the side opposite to said opening forms said guide track.

6. The device according to claim 1, wherein said selection sleeve of said device arming means is integral to a selection knob angularly displaceable in only one direction about said longitudinal axis relative to said outer body and comprises a pair of legs longitudinally extending in said outer body and engaging with a cam ratchet, on which said third cam means are formed, for causing said third cam means to angularly displace in the opposite direction to the angular displacement caused by them.

7. The device according to claim 6, wherein said third cam means have a profile formed by an upward portion, a downward portion and a portion extending along an arc of circumference from a beginning of said upward portion and an end of said downward portion, said upward portion and downward portion being inclined in opposite directions, said slide comprising at least a cam follower button contacting said profile, the sliding of said button along said circumferential portion being controlled by the angular displacement of said selection sleeve, the sliding along said upward portion and downward portion being controlled by the axial motion of said slide.

8. The device according to claim 7, wherein said cam ratchet is a tubular element with a side surface on which said third cam means are formed, a toothed ring being formed in said cam ratchet with which a corresponding toothed end of said legs engages, the teeth of said toothed ring being so profiled as to allow said toothed end to slide along said toothed ring in one direction only.

9. The device according to claim 1, wherein a pair of legs axially extends from said transfer sleeve of said cam transmission means, the ends of said legs abutting on said slide, whereby a backward motion of the slide causes a corresponding sliding of said transfer sleeve in opposition to third elastic means placed between said transfer sleeve and said inner body.

10. The device according to claim 1, wherein said inner body comprises a piston sleeve having one end connected to an end of a barrel of the syringe and provided at the other end with a collar, a toothed ring being formed in said collar with which a corresponding toothed end of a pair of arms engages, said arms extending from a selection knob, the teeth of said toothed ring being so profiled as to allow said toothed end to slide along said toothed ring in one direction only.

11. The device according to claim 10, wherein reference marks are provided on an outer surface of said collar and on said selection knob designed for being selectively aligned as a result of successive rotations of the selection knob from said rest position to said first armed position and from said first armed position to said second armed position.

12. The device according to claim 1, wherein said piston means comprise a piston rod slidingly engaged in a barrel of the syringe and a tubular housing axially extending from said piston rod and housing said first elastic means, said tubular housing being arranged in said selection knob around a boss thereof, said first elastic means comprising a spring around said boss, a bayonet connection being provided between said boss and said tubular housing releasable as a result of an angular displacement of said selection knob to said first armed position.

13. The device according to claim 12, wherein said bayonet connection is formed by a substantially T-shaped end of said boss and by two diametrically opposed inner projections of said housing, which are mutually engaged when the device is in its rest position and disengageable following an angular displacement of the selection knob toward said first armed position.

14. The device according to claim 12, wherein said second guide means extend outwardly from said tubular housing.

15. The device according to claim 1, wherein flexible tines project from an outer surface of the slide for abutting against the end edge of said outer body, a contact surface of said tines with said edge being inclined to allow sliding of said edge thereon, whereby a moderate force exerted by the user is required to deflect the tines sufficiently to allow the slide to move axially inside the outer body.

16. The device according to claim 1, wherein said needle is covered by a needle shield and a needle shield remover is removably secured to the outer body and is provided with an inner tubular grip fit for engaging with the needle shield, whereby, by pulling the needle shield remover before the first dose is administered, the user can remove the needle shield and free the needle for the injection.

17. The device according to claim 1, wherein at least one opening is formed on said outer body lined up to at least one transparent inspection window for checking a drug delivery status.

* * * * *